United States Patent [19]

Alexander et al.

[11] 4,244,880

[45] Jan. 13, 1981

[54] ANTHRACYCLINE SYNTHESIS

[75] Inventors: Jose Alexander, Kansas City; Lester A. Mitscher, Lawrence, both of Kans.

[73] Assignee: University of Kansas Endowment Association, Lawrence, Kans.

[21] Appl. No.: 912,842

[22] Filed: Jun. 5, 1978

[51] Int. Cl.$^3$ .................. C07C 50/18; C07C 50/16; C07C 101/80; C07C 103/75
[52] U.S. Cl. ................... 260/383; 260/376; 260/377; 260/365; 568/633; 560/52
[58] Field of Search ............... 260/376, 668 F, 611 F, 260/383, 365, 377, 393

[56] References Cited

U.S. PATENT DOCUMENTS

| 3,173,913 | 3/1965 | van der Stelt | 260/668 F |
|---|---|---|---|
| 4,012,448 | 3/1977 | Smith et al. | 260/365 |
| 4,021,457 | 5/1977 | Kende et al. | 260/383 |
| 4,116,981 | 9/1978 | Kende | 260/376 |

OTHER PUBLICATIONS

*Chemical Abstracts,* vol. 83, #210755g, Wayne et al., "Electrochemical Reactions of Organic Compounds in Ammonia III Reductive Alkylation of Quinoline", 1975.
*Chemical Abstracts,* vol. 81, #37348, Tashiro et al., "Positional Protective Groups on Aromatic Rings I New Preparative Method for Halophenols With Tert-butyl or Benzyl Group as a Protective Group," 1974.
*Chemical Abstracts,* vol. 86, #120900r, Meider et al., "Specific Ortho–bromination I Preparation of Ortho–bromo Substituted benzenes, " 1977.
*Journal of the American Chemical Society,* vol. 99, p. 5513, "Synthetic Approaches to Adriamycin", Kelly et al., 1977.
*Tetrahedron Letters,* No. 28, p. 2323, "A Regiospecific Synthesis of Anthracyclinones", Swenton et al., 1977.
*Journal of Organic Chem.,* vol. 41, No. 13, pp. 2296-2301, "Daunomycinone Analogues via Diels–Alder Reaction", Lee et al., 1976.

*Primary Examiner*—Winston A. Douglas
*Assistant Examiner*—Raymond K. Covington
*Attorney, Agent, or Firm*—Finnegan, Henderson, Farabow & Garrett

[57] ABSTRACT

A process for synthesizing the 7-substituted or unsubstituted 5,12-dihydroxy-1,2,3,4,6,11-hexahydro-2,6,11-trioxonaphthacene precursors for doxorubicin and related compounds from butadiene and p-benzoquinone and intermediates useful in the synthesis.

18 Claims, No Drawings

ANTHRACYCLINE SYNTHESIS

The present invention relates generally to a technique for synthesizing doxorubicin and related compounds such as daunomycin, 7-demethoxy daunomycin and carminomycin, and the aglycones thereof. More particularly, the present invention relates to a new and improved process for the production of 7-substituted or unsubstituted 5,12-dihydroxy-1,2,3,4,6,11-hexahydro-2,6,11-trioxonaphthacenes which are well known and established intermediates in the synthesis of doxorubicin and related compounds. The present invention also pertains to intermediates useful in the synthesis process.

BACKGROUND OF THE INVENTION

Doxorubicin is a known anthracycline antibiotic described for example in U.S. Pat. No. 3,590,028. Doxorubicin, and the closely related compound daunomycin, are antineoplastic agents of established clinical utility. Doxorubicin hydrochloride, available from Adria Laboratories, Inc., under the trademark Adriamycin(R), has been approved by the Food and Drug Administration for use in clinical research, and is one of the most powerful anticancer drugs available against numerous forms of cancer.

At present, doxorubicin is produced commercially from a soil fungus by a fermentation process. A suitable fermentation technique for preparing doxorubicin is described in U.S. Pat. No. 3,590,028. Such techniques are inherently expensive and limit the types of molecules that can be produced. Because of the inherent disadvantages of presently available commercial techniques for producing doxorubicin and related compounds, substantial effort has been devoted to developing processes for producing such compounds by chemical synthesis.

Techniques for the synthesis of anthracycline antibiotics such as doxorubicin are known. See, e.g., Wong et al., *Canadian Journal of Chemistry*, Vol. 51, page 466 (1973); Acton et al., *Journal of Medicinal Chemistry*, Vol. 17, No. 6, page 659 (1974); Kende et al., *Journal of the American Chemical Society*, Vol. 97, No. 15, page 4425 (1975) and Vol. 98, No. 7, page 1967 (1976); Sih et al., *Tetrahedron Letters*, page 3385 (1976); Swenton et al., *Tetrahedron Letters*, pages 2383 (1977); and Kelly et al., *Journal of the American Chemical Society*, Vol. 99, page 5513 (1977). None of the known techniques for the total synthesis of anthracycline antibiotics such as doxorubicin have yet been proven to be commercially successful. Because of the demand for, and scarcity of, these compounds, a suitable synthesis technique is highly desired.

The present invention provides a practical technique for synthesizing doxorubicin and related compounds, from readily available and inexpensive starting materials. Specifically, and in accordance with the present invention, doxorubicin and similar compounds may be synthesized from butadiene and p-benzoquinone. In addition, the present invention provides valuable intermediate compounds that are useful in synthesizing doxorubicin and related compounds.

SUMMARY OF THE INVENTION

Anthracycline antitumor antibiotics such as doxorubicin, daunomycin, 7-demethoxy daunomycin and carminomycin, including their aglycones, are conventionally prepared from known trioxonaphthacene intermediates, in particular, 7R-5,12-dihydroxy-1,2,3,4,6,11-hexahydro-2,6,11 trioxonaphthacenes in which R is H, OH or $OCH_3$, according to well known techniques more specifically described below. For the purposes of this summary, the process will be described as it relates to the production of the trioxonaphthacene where $R = OCH_3$, the precursor for doxorubicin, but it is to be understood the process is equally applicable to the production of the analogous well known intermediates for the synthesis of the other anthracyclines.

The trioxonaphthacene is synthesized by first preparing 1,4,4a,5,8,8a-cis-hexahydro-5,8-dioxonaphthalene, a well-known reaction product of butadiene and p-benzoquinone and then alkylating it to prepare the 1,4 dihydronaphthalene derivative.

In accordance with the present invention and as more fully described below, the reaction product can be alkylated with a $C_1$ to $C_6$ alkyl or benzylated with a benzyl radical to prepare 5,8-dialkoxy or 5,8-dibenzyloxy-1,4-dihydronaphthalene. For the purpose of this discussion, however, it is assumed that the product is methylated to prepare 5,8-dimethoxy-1,4-dihydronaphthalene. This compound is then hydrated to produce 2-hydroxy-5,8-dimethoxy-1,2,3,4 tetrahydronaphthalene, which is in turn alkylated to produce 5,8-dimethoxy-2-t-butoxy-1,2,3,4-tetrahydronaphthalene. This compound is brominated to provide a snythetically useful mixture of 5,8-dimethoxy-6-bromo-2-t-butoxy-1,2,3,4-tetrahydronaphthalene and 5,8-dimethoxy-7-bromo-2-t-butoxy-1,2,3,4-tetrahydronaphthalene.

This mixture is then converted to its lithio analog and reacted with dimethyl 3-methoxyphthalate to produce 5,8-dimethoxy-2-t-butoxy-6- and 7-(3-methoxy-2-carbomethoxy) benzoyl-1,2,3,4-tetrahydronaphthalene. Cyclization with boron trichloride or boron tribromide results in removal of the blocking groups with the formation of 7-methoxy-2,5,12-trihydroxy-1,2,3,4,6,11-hexahydro-6,11-dioxonaphthacene. Oxidation leads to the well known intermediate for the production of doxorubicin, 7-methoxy-5,12-dihydroxy-1,2,3,4,6, 11-hexahydro-2,6,11 trioxonaphthacene.

The present invention also provides valuable intermediates useful in the synthesis, including those having the formulas:

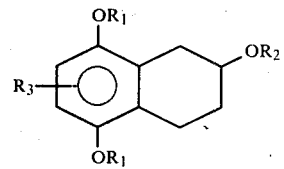

A.

wherein
$R_1$ is a $C_1$–$C_6$ alkyl group or $CH_2C_6H_5$;
$R_2$ is H or $C(CH_3)_3$; and
$R_3$ is H, Br or Li.

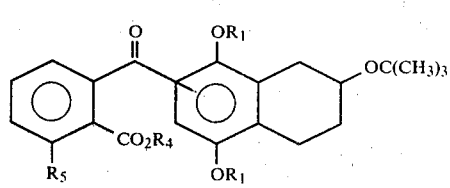

B.

wherein
$R_1$ and $R_4$ are $C_1$–$C_6$ alkyl groups or $CH_2C_6H_5$; and $R_5$ is hydrogen, methoxy or acetoxy.

DESCRIPTION OF PREFERRED EMBODIMENTS

In the synthesis of the present invention, commercially available and inexpensive butadiene and p-benzoquinone are allowed to react under the normal conditions of the Diels-Alder reaction [See O. Diels and K. Alder, Ber., 62 page 2337 (1929) to give the well-known adduct, 1,4,4a,5,8,8a-cis-hexahydro-5,8-dioxonaphalene, having the following formula:

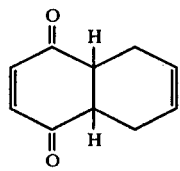

(1)

Alkylation with a $C_1$–$C_6$ alkyl group or benzylation with a benzyl group under alkaline conditions produces the non-conjugated dihydro-naphthalene derivatives of the following formula:

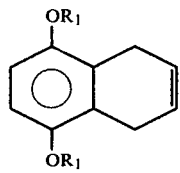

(2)

in which $R_1$ represents an alkyl group of from 1 to 6 carbon atoms or the benzyl moiety. The compounds can be defined as 5,8-dialkoxy or 5,8-dibenzyloxy-1,4-dihydronaphthalene.

Hydration of the double bond, as for example under hydroboration-oxidation conditions, produces the tetrahydronaphthol compound 5,8-dialkoxy or 5,8-dibenzyloxy-2-hydroxy-1,2,3,4 tetrahydronaphthalene of the following formula:

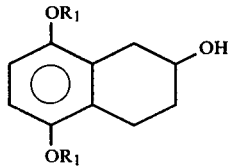

(3)

in which $R_1$ is the same as defined above.

Etherification to produce the t-butyl ether is accomplished by acidification in the presence of an appropriate source of t-butyl carbonium ion resulting in the formation of 5,8-dialkoxy or 5,8-dibenzyloxy-2-t-butoxy-1,2,3,4-tetrahydronaphthalene having the following formula:

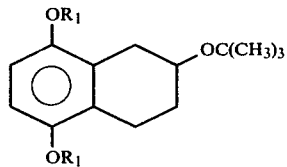

(4)

in which $R_1$ is the same as defined above.

Bromination produces a mixture of monobromides which may be separated or, in many applications, conveniently used without separation. The bromides have the following formula:

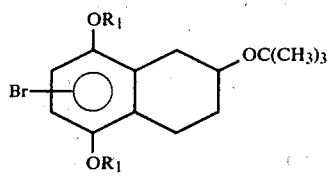

(5)

in which $R_1$ is the same as defined above. These compounds may be defined as 5,8-dialkoxy or 5,8-dibenzyloxy-6- and 7 -bromo-2-t-butoxy-1,2,3,4-tetrahydronaphthalene.

Lithiation with n-butyl lithium produces the corresponding organometallic reagents of the following formula:

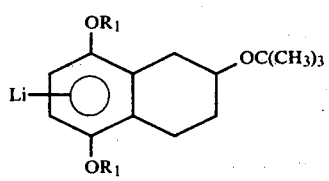

(6)

Reaction of the organometallic reagents with dimethylphthalate, dimethyl 3-acetoxyphthalate, or dimethyl 3-methoxyphthalate produces the corresponding aryl ketones of the following formula:

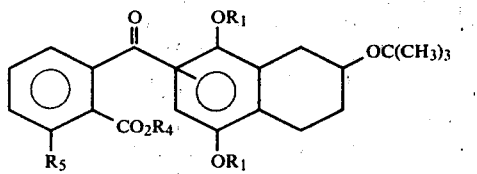

(7)

in which $R_1$ is the same as defined above, $R_4$ is the same as $R_1$ and $R_5$ represents hydrogen, methoxy or acetoxy.

The aryl ketones are cyclized with a Friedel-Crafts catalyst, of which $BCl_3$ or $BBr_3$ are particularly convenient, to produce the deblocked naphthacene derivatives of the following formula:

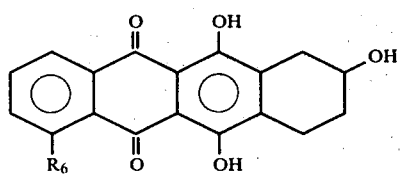

(8)

in which $R_6$ represents H, OH or $OCH_3$. These compounds may be oxidized, by the method of Lee et. al., J. Org. Chem., 41, page 2296 (1976) to the corresponding ketones of the following formula:

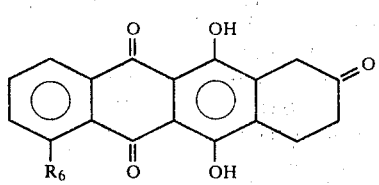
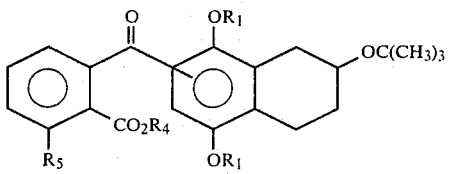

in which $R_6$ is the same as defined above.

Such ketones are established intermediates in the total synthesis of anthracycline antitumor antibiotics such as daunomycin, 7-demethoxy daunomycin, carminomycin and doxorubicin (see A. S. Kende et al., *J. Amer. Chem. Soc.*, 98, page 1967 (1976). More particularly, the ketone intermediate (9) when $R_6$ is H (5,12-dihydroxy-1,2,3,4,6,11-hexahydro-2,6,11-trioxonaphthacene) leads to 7-demethoxy daunomycin; the ketone intermediate when $R_6$ is OH (5,7,12-trihydroxy-1,2,3,4,6,11-hexahydro-2,6,11-trioxonaphthacene) leads to carminomycin; and the ketone intermediate when $R_6$ is $OCH_3$ (7-methoxy-5,12-dihydroxy-1,2,3,4,6,11-hexahydro-2,6,11 trioxonaphthacene) leads to daunomycin and doxorubicin according to the procedures set forth in this article.

The process of the present invention, previously described, results in the formation of a number of useful intermediates. Exemplary of useful intermediates are those having the formula:

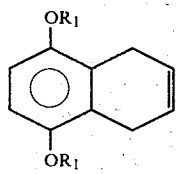

in which $R_1$ is $C_1$-$C_6$ alkyl or benzyl. An example of an intermediate corresponding to the above-identified formula in which $R_1$ is methyl is 5,8-dimethoxy-1,4-dihydronaphthalene.

Also useful as intermediates are compounds of the formula:

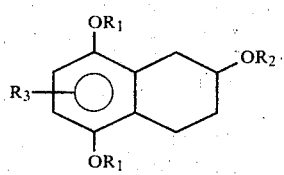

in which $R_1$ is as defined above; $R_2$ is H or $C(CH_3)_3$; and $R_3$ is H, Br or Li.

Examples of intermediates corresponding to the above-identified formula include: (a) 2-hydroxy-5,8-dimethoxy 1,2,3,4 tetrahydronaphthalene, the compound when $R_1$ is methyl and $R_2$ and $R_3$ are hydrogen; (b) 5,8-dimethoxy-2-t-butoxy-1,2,3,4-tetrahydronaphthalene, the compound when $R_1$ is methyl, $R_2$ is t-butyl and $R_3$ is hydrogen; (c) 5,8-dimethoxy-6- and 7-bromo-2-t-butoxy-1,2,3,4-tetrahydronaphthalene, the compound when $R_1$ is methyl, $R_2$ is t-butyl and $R_3$ is bromine; and (d) 5,8-dimethoxy-2-t-butoxy-6- and 7-lithio-1,2,3,4-tetrahydronaphthalene, the compound when $R_1$ is methyl, $R_2$ is t-butyl and $R_3$ is lithium.

Other useful intermediates are compounds of the formula:

in which $R_1$ is as defined above; $R_4$ is the same as $R_1$; and $R_5$ is hydrogen, methoxy or acetoxy.

Examples of intermediates corresponding to the above-identified formula include 5,8-dimethoxy-2-t-butoxy-6- or 7- (2-methoxycarbonyl) benzoyl-1,2,3,4-tetrahydronaphthalene, the compound when $R_1$ and $R_4$ are methyl and $R_5$ is H; 5,8-dimethoxy-2-t butoxy-6- or 7-(3-methoxy-2-methoxycarbonyl) benzoyl-1,2,3,4-tetrahydronaphthalene, the compound when $R_1$ and $R_4$ are methyl and $R_5$ is methoxy; and 5,8-dimethoxy-2-t-butoxy-6- or 7-(3 acetoxy-2-methoxycarbonyl) benzoyl-1,2,3,4-tetrahydronaphthalene, the compound when $R_1$ and $R_4$ are methyl and $R_5$ is acetoxy.

The following examples further illustrate preferred embodiments of the present invention. The examples should in no way be considered limiting, but are merely illustrative of the various features of the present invention.

EXAMPLE 1 p-Benzoquinone (10.8 g) was dissolved in benzene (100 ml) and cooled in an ice bath. Condensed butadiene (ca. 15 ml) was added and the mixture was stoppered in a pressure vessel and then shaken at 50° for 23 hours. After cooling the pressure vessel was opened and the benzene was evaporated. The residue weighing 16.6 g was the pure monoadduct (1,4,4a,5,8,8a-cis-hexahydro-1,4-dioxonaphthalene) corresponding to formula 1 above. A sample crystallized from light petrol melts at 58°. (Reported 58°, Diels and Alder, Ber., 62, 2337 (1929).

The product was analyzed and had the following characteristics: The nuclear magnetic resonance spectrum (NMR) has the following peaks (CDCl$_3$) δ1.8–2.9 (4H, allylic H), 3.1–3.4 (2H, m, tertiary H), 5.71 (2H, s, olefinic H), 6.70 (2H, s, olefinic H). The infra red (IR) spectrum has the following peaks (KBr) 3040, 2890, 1655, 1600, 1420, 1255, 1083, 834 cm$^{-1}$.

EXAMPLE 2

Alkylation to produce the compound of formula 2 where $R_1$ is methyl, namely 5,8-dimethoxy-1,4-dihydronaphthalene was accomplished as follows:

The Diels-Alder adduct of Example 1 (38 g) dissolved in acetone (200 ml) was refluxed with dimethyl sulfate (65 g) and potassium carbonate (80 g) for 18 hours. The potassium salts were filtered off and washed with acetone. The combined filtrate and washings on evaporation gave a thick liquid (43 g) which solidified on standing. It was crystallized from light petrol. The first crop was 19.45 g. Another 17.2 g more was obtained from the mother liquor on subsequent crystallizations. m.p. 50°.

The compound had the following characteristics: NMR (CDCl$_3$) δ3.25 (4H, s, allylic H), 3.76 (6H, s, OCH$_3$), 5.83 (2H, s, olefinic H), and 6.60 (2H, s, aromatic H). IR (nujol) 1610, 1485, 1463, 1252, 1096, 1081 cm$^{-1}$.

EXAMPLE 3

The 5,8-dimethoxy-2-hydroxy-1,2,3,4-tetrahydronaphthalene compound of formula 3 may be prepared as follows:

The olefin of Example 2 (7 g) was dissolved in THF (30 ml) in a flask fitted with an addition funnel and reflux condenser and stoppered with rubber septa. It was purged with dry nitrogen and an atmosphere of nitrogen was maintained throughout the experiment. The solution was cooled in ice and a 1 M solution of diborane in THF (37 ml, 1 mole equiv.) was added dropwise during ½ hour. It was then kept stirred at room temperature for 2 hours. 5 ml of water was added with cooling to decompose the excess hydride.

After introducing 25 ml of a 3 M solution of sodium hydroxide, 13 ml of 30° $H_2O_2$ was added dropwise at such a rate that the temperature of the reaction mixture did not rise above 50°. It was then heated at 50° (bath) for 1½ hours and left stirring at room temperature overnight. The aqueous layer was saturated with KCl and the organic layer was separated. The aqueous layer was extracted with ether once.

The combined organic extract was dried over $K_2CO_3$ and evaporated. The residue weighing 6.55 g was the pure hydroxy compound. Crystallization from benzene-light petrol furnished 5.7 g of the pure secondary alcohol. m.p. 130°–131.5°.

The product had the following characteristics: NMR ($CDCl_3$) $\delta$1.6–2.1 (3H, multiplet, $C_3\underline{H}$ and $O\underline{H}$), 2.2–3.2 (4H, benzylic H, multiplet), 3.56 (6H, s, $OC\underline{H}_3$), 3.8–4.3 (1H, multiplet, $C\underline{H}$-OH) and 6.60 (2H, s, aromatic H). IR (nujol) 3360–3280, 1610, 1480, 1462, 1376, 1255, 1093, 1075, 1035, 780, 708 cm$^{-1}$.

EXAMPLE 4

The t-butyl ether of 5,8-dimethoxy-2-hydroxy-1,2,3,4-tetrahydronaphthalene, a compound of formula 4, was prepared as follows:

The alcohol of Example 3 (30 g) suspended in methylene chloride (100 ml) was cooled in dry ice-alcohol bath to $-20°$. Boron trifluoride-etherate (3.0 ml) and 100% $H_3PO_4$ (1.5 ml) were added to it. Condensed isobutylene (100 ml) was added to the mixture and shaken at room temperature for 16 hours. All the suspended solid had disappeared during this time. The reaction mixture was washed 3 times with water and then dried over sodium sulfate. The residue on evaporation was diluted with light petrol (125 ml) and filtered through a small bed of alumina to remove a trace of unreacted starting material. The filtrate on evaporation furnished the pure t-butyl ether, 5,8-dimethoxy-2-t-butoxy-1,2,3,4-tetrahydronaphthalene, as a colorless thick syrup (35.2 g) (92.6% yield).

The ether had the following characteristics:
NMR ($CDCl_3$) $\delta$1.21 (9H, s, t-butyl), 1.4–3.3 (6H, multiplet, alicyclic H), 3.75 (6H, s, $OC\underline{H}_3$), and 6.62 (2H, s, aromatic H). IR (film) 2290, 2822, 1603, 1480, 1438, 1390, 1358, 1250, 1190, 1100, 1040, 982, 903 cm$^{-1}$.

EXAMPLE 5

5,8-Dimethoxy-6- and 7-bromo-2-t-butoxy-1,2,3,4-tetrahydronaphthalene compounds of formula 5, were prepared as follows:

To the t-butyl ether of Example 4 (35.1 g) dissolved in chloroform (150 ml), acetamide (8 g) was added and stirred to dissolve. The solution was then cooled in ice. A solution of bromide (21.7 g) in chloroform (30 ml) was added to the ice cold solution of the t-butyl ether with stirring during 2 hours. It was kept stirred at 0° for an additional 0.5 hr after the addition of bromine. The chloroform solution was then washed with water (2×), sodium bisulfite (2×) and water (2×). It was dried over sodium sulfate and evaporated. The residue was a pale yellow liquid.

It was dissolved in light petrol (200 ml) and filtered through alumina (Merck) 60 g. The filtrate and light petrol washings were evaporated to furnish the pure monobromo compounds. After vacuum drying at 40°/0.3 mm for 1 hour, the compounds weighed 42.7 g, (93.7% yield).

The monobromo compounds had the following characteristics. NMR ($CDCl_3$) $\delta$1.23 (9H, s, t-butyl), 1.6–3.3 (6H, multiplet, alicyclic H), 3.76 (6H, s, $OC\underline{H}_3$) and 6.77 (1H, s, aromatic H). MS m/e 342, 344 (M+), 288, 286 (H+-isobutylene), 268, 270 (M+-tBuOH), 207 ([M+-Br+isobutylene)]), etc.

EXAMPLE 6

5,8,-Dimethoxy-2-t-butoxy-6- or 7-(2-methoxycarbonyl) benzoyl-1,2,3,4-tetrahydronaphthalene compounds of formula (7) where $R_5$ is hydrogen, were prepared as follows:

The nuclear bromo derivative of the t-butyl ether of Example 5 (34.3 g) was dissolved in 500 ml of freshly distilled (from benzophenone ketyl) tetrahydrofuran in a 3-necked flask fitted with a thermometer and dropping funnel. The solution was cooled to $-95°$ to $-100°$ in a diethyl ether-liquid nitrogen bath. The n-butyl lithium in THF (68 ml of 1.5 M solution, 1.1 equivalents) was added to the stirred solution maintaining the temperature at $-95°$ to $-90°$. It was then allowed to warm up to $-80°$ during 45 min. A solution of dimethyl phthalate (23 g, 1.2 equiv.) in dry THF (25 ml) was then added during ½ hour. When the addition was complete, the temperature of the reaction mixture was $-40°$. It was then left stirring at room temperature overnight. Acetic acid (10 ml) was added and the THF was evaporated. The residue was taken in ether and washed with water, aqueous sodium bicarbonate (2×) and water (2×). The ether extract was dried over sodium sulfate and evaporated. The residue weighing 51.05 g was a thick yellow liquid. It contained, in addition to the condensation product, small amounts of dimethyl phthalate and the starting t-butyl ether.

This sample (25 g) on high performance liquid chromatography on a Sigel column using ethyl acetate-chloroform (1:9) as eluent furnished 16.3 g of the pure compound as a mixture of isomers. This set to a resinous solid on standing (yield 65.2%). However, it is not necessary to purify the condensation product for the next (cyclization) step. The cyclization product is highly insoluble and can be purified easily by solvent washing.

The product of this example had the following characteristics:

NMR ($CDCl_3$) $\delta$1.20 (9H, s, t-butyl), 1.5–3.2 (4H, multiplet), 3.26 (3H, s, $CO_2C\underline{H}_3$), 3.65 and 3.73 (3H each, singlets, $OC\underline{H}_3$), 6.95 (1H, s, aromatic) and 7.36 (4H, quartet, J=4 Hz, aromatic). IR 1730, 1610, 1595, 1460, 1402, 1270, 1220 cm$^{-1}$. Mass spectrum (MS) m/e 426 (M+), 425 (M+-1, 379, 369, (M+-57, 332 and 162 (base peak

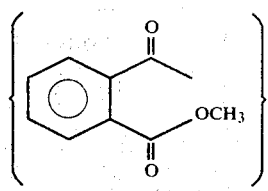

+).

EXAMPLE 7

2,5,12-Trihydroxy-1,2,3,4,6,11-hexahydro-6,11-dioxonaphthacene, a compound of formula 8 where $R_6$ is H was then prepared as follows:

The ortho-keto ester of Example 6 (0.5 g) was dissolved in methylene chloride (50 ml) and cooled in ice. Boron trichloride gas was passed into the solution until there was an excess. It was stirred at room temperature until TLC showed that there was no more starting material and all the compound was converted to the tetracyclic compound (48 hours). When the reaction was complete, the methylene chloride and excess $BCl_3$ were evaporated off in vacuum.

The residue was triturated with 0.5 N hydrochloric acid (30 ml) and filtered. The red solid was the practically pure hydroxy compound (0.35 g) 96.4% yield.

The dioxonaphthacene compound had the following characteristics:

NMR ($CF_3CO_2H$) $\delta2.0-3.3$ (6H, multiplet), 5.75 (1H, multiplet), 7.92 (2H, multiplet, aromatic) and 8.4 (2H, multiplet, aromatic). IR (KBr) 3420, 1618, 1580, 1395, 1245 cm$^{-1}$. Ultraviolet (UV) (EtOH)$\lambda_{max}$ ($\epsilon$), 513 (4802), 482 (6985), 456 (6086), 326 (2439), 287 (6369), 256 (27995), 252 (28508) nm. MS m/e 310 (M+), 292 (M+-18), 291 (M$^{30}$-18-1), 290

EXAMPLE 8

A scond method for the preparation of 2,5,12-trihydroxy-1,2,3,4,6,11-hexahydro-6,11-dioxonaphthacene is as follows:

The keto ester of Example 6 (1.3 g) dissolved in dichloromethane (30 ml) was cooled to −70°. A 1 M solution of $BBr_3$ in methylene chloride (20 ml) was added dropwise. The reaction mixture was then allowed to warm up to −15°. The slow appearance of the cyclic alcohol as well as the bromo compound could be detected on TLC (developed with ethyl acetate-chloroform (2:8). After allowing it to stand in the refrigerator (ca. −10°) for 16 hours, the reaction mixture was decomposed by adding water. The multiphase mixture was filtered and the solid washed with water. The filtrate was separated into the two layers. The organic layer was washed with water and evaporated to give 0.8 g of the desired alcohol. This was purified by dissolving the residue in methylene chloride and crystallizing the desired alcohol by adding light petrol.

EXAMPLE 9

5,8-Dimethoxy-2-t-butoxy-6- and 7-(3-methoxy-2-carbomethoxy) benzoyl-1,2,3,4-tetrahydronaphthalene, a compound of formula 7 where $R_5$ is $OCH_3$ was prepared as follows:

To the lithio derivative of the t-butyl ether prepared as in Example 6 (from 8 g of bromo compound) was added a solution of dimethyl 3-methoxyphthalate (4.9 g) in dry THF (15 ml) dropwise over 0.5 hr. The reaction was stirred at room temperature overnight, acetic acid (2 ml) was added and the THF was evaporated. The residue was worked up as in Example 6 to give 10.2 g of oily product which was used in the next example without further purification.

EXAMPLE 10

7-Methoxy-2,5,12-trihydroxy-1,2,3,4,6,11-hexahydro-6,11-dioxonaphthacene, a compound of formula 8 where $R_6$ is $OCH_3$ was prepared as follows:

The aryl ketone of Example 9 (5.0 g) was dissolved in 250 ml of methylene chloride and cooled in ice. Boron trichloride gas was passed into the solution until there was an excess. The reaction mixture was stirred at room temperature for two days and the volatiles were removed under reduced pressure. The residue was triturated with 0.5 N hydrochloric acid and filtered. The red solid was purified by preparative scale hplc chromatography using silica gel and methylene chloride/methanol as solvent followed by crystallization from methylene chloride. The product had the following characteristics:

IR peaks at 3420, 1620, 1580 cm$^{-1}$.
MS m/e 340 (M+), 322 (M+-18), 321 and 320.

EXAMPLE 11

2,5,7,12-Tetrahydroxy-1,2,3,4,6,11-hexahydro-6,11-dioxonaphthacene, a compound of formula 8 where $R_6$ is OH can be prepared according to the procedures of Examples 9 and 10, but using dimethyl 3-acetoxyphthalate in place of dimethyl 3-methoxyphthalate.

EXAMPLE 12

When a sample of the alcohol of Example 10 (20 mg) was oxidized according to the procedure of Lee et al., *J. Org. Chem.*, 41, page 2302, and the product crystallized from pyridine, the product had mp 249–250 and was identical in chromatographic and spectroscopic properties to 7-methoxy-b 5,12-dihydroxy-1,2,3,4,6,11-hexahydro-2,6,11-trioxonaphthacene as described by A. S. Kende et al., *J. Am. Chem. Soc.*, 98, page 1968 (1976).

This known intermediate can then be used to produce daunomycin or doxorubicin according to the procedure set forth in this article.

Similarly, the compound of Example 7 can be oxidized to produce 5,12 dihydroxy-1,2,3,4,6,11-hexahydro-2,6,11 trioxonaphthacene, a known precursor for 7-demethoxy daunomycin and the compound of Example 11 oxidized to produce 5,7,12-trihydroxy-1,2,3,4,6,11-hexahydro-2,6,11-trioxonaphthacene, a known precursor for carminomycin.

Although the present invention has been described in connection with preferred embodiments, it is understood that modifications and variations may be resorted to without departing from the spirit and scope of the invention. Such modifications are considered to be within the purview and scope of the invention and the appended claims.

What is claimed is:

1. A process for producing 5,12-dihydroxy-1,2,3,4,6,11-hexahydro-2,6,11-trioxonaphthacene comprising:
   a. reacting p-benzoquinone with butadiene to produce 1,4,4a,5,8,8a-cis-hexahydro-5,8-dioxoanaphthalene;
   b. alkylating with a $C_1$–$C_6$ alkyl group or benzylating with a benzyl group the reaction product of (a) to produce 5,8-dialkoxy or 5,8-dibenzyloxy-1,4-dihydronaphthalene;

c. hydrating the compound of (b) to produce 5,8-dialkoxy or 5,8-dibenzyloxy-2-hydroxy-1,2,3,4-tetrahydronaphthalene;
d. etherification of the compound of (c) in the presence of a t-butyl carbonium ion to produce 5,8-dialkoxy or 5,8-dibenzyloxy-2-t-butoxy-1,2,3,4-tetrahydronaphthalene;
e. brominating the ether of (d) to produce 5,8-dialkoxy or 5,8-dibenzyloxy-6-and 7-bromo-2-t-butoxy-1,2,3,4-tetrahydronaphthalene;
f. lithiating the compound of (e) followed by acylation of the lithio derivative with dimethyl phthalate to produce 5,8-dialkoxy or 5,8-dibenzyloxy 2-t-butoxy-6 or 7-(2-methoxycarbonyl) benzoyl-1,2,3,4-tetrahydronaphthalene;
g. cyclization and deprotection of the compound of (f) with a Fiedel-Crafts catalyst to produce 2,5,12-trihydroxy-1,2,3,4,6,11-hexahydro-6,11-dioxonaphthacene; and
h. oxidation of the compound of (g) to produce 5,12-dihydroxy 1,2,3,4,6,11-hexahydro-2,6,11-trioxonaphthacene.

2. A process for producing 7-methoxy-5,12-dihydroxy 1,2,3,4,6,11-hexahydro-2,6,11-trioxonaphthacene comprising:
a. reacting p-benzoquinone with butadiene to produce 1,4,4a,5,8,8a-cis-hexahydro-5,8-dioxonaphthalene;
b. alkylating with a $C_1$–$C_6$ alkyl group or benzylating with a benzyl group to the reaction product of (a) to produce 5,8-dialkoxy or 5,8-dibenzyloxy-1,4-dihydronaphthalene;
c. hydrating the compound of (b) to produce 5,8-alkoxy or 5,8-dibenzyloxy-2-hydroxy-1,2,3,4 tetrahydronaphthalene;
d. etherification of the compound of (c) in the presence of a t-butyl carbonium ion to produce 5,8-dialkoxy or 5,8-dibenzyloxy-2-t-butoxy-1,2,3,4-tetrahydronaphthalene;
e. brominating the ether of (d) to produce 5,8-dialkoxy or 5,8 -dibenzyloxy-6- and 7-bromo-2-t-butoxy-1,2,3,4-tetrahydronaphthalene;
f. lithiating the compound of (e) followed by acylation of the lithio derivative with dimethyl 3-methoxyphthalate to produce 5,8-dialkoxy or 5,8-dibenzyloxy 2-t-butoxy-6 or 7-(3-methoxy-2-methoxycarbonyl) benzoyl-1,2,3,4-tetrahydronaphthalene;
g. Cyclization and deprotection of the compound of (f) with a Friedel-Crafts catalyst to produce 7-methoxy-2,5,12-trihydroxy-1,2,3,4,6,11-hexahydro-6,11-dioxonaphthacene; and
h. oxidation of the compound of (g) to produce 7-methoxy-5,12-dihydroxy 1,2,3,4,6,11-hexahydro-2,6,11-trioxonaphthacene.

3. A process for producing 5,7,12-trihydroxy 1,2,3,4,6,11-hexahydro-2,6,11-trioxonaphthacene comprising:
a. Reacting p-benzoquinone with butadiene to produce 1,4,4a,5,8,8a-cis-hexahydro-5,8-dioxonaphthalene;
b. alkylating with a $C_1$–$C_6$ alkyl group or benzylating with a benzyl group the reaction product of (a) to produce 5,8-dialkoxy or 5,8-dibenzyloxy-1,4-dihydronaphthalene;
c. hydrating the compound of (b) to produce 5,8-dialkoxy or 5,8-dibenzyloxy-2-hydroxy-1,2,3,4-tetrahydronaphthalene;
d. etherification of the compound of (c) in the presence of a t-butyl carbonium ion to produce 5,8-dialkoxy or 5,8-dibenzyloxy-2-t-butoxy-1,2,3,4-tetrahydronaphthalene;
e. brominating the ether of (d) to produce 5,8-dialkoxy or 5,8-dibenzyloxy-6- and 7-bromo-2-t-butoxy-1,2,3,4-tetrahydronaphthalene;
f. lithiating the compound of (e) followed by acylation of the lithio derivative with dimethyl 3-acetoxyphthalate to produce 5,8-dialkoxy or 5,8-dibenzyloxy-2-t-butoxy-6 or 7-(3-acetoxy-2-methoxycarbonyl) benzoyl-1,2,3,4-tetrahydronaphthalene;
g. cyclization and deprotection of the compound of (f) with a Friedel-Crafts catalyst to produce 2,5,7,12-tetrahydroxy-1,2,3,4,6,11-hexahydro-6,11-dioxonaphthacene; and
h. oxidation of the compound of (g) to produce 5,7,12-trihydroxy-1,2,3,4,6,11-hexahydro-2,6,11-trioxonaphthacene.

4. A compound having the formula:

[Structure with $OR_1$, $OR_2$, $R_3$, $OR_1$ substituents on bicyclic ring]

wherein:
$R_1$ is a $C_1$ to $C_6$ alkyl group or benzyl;
$R_2$ is H or $C(CH_3)_3$; and
$R_3$ is H, Br or Li.

5. The compound of claim 4 in which $R_1$ is methyl, $R_2$ is hydrogen and $R_3$ is hydrogen.

6. The compound of claim 4 in which $R_1$ is methyl, $R_2$ is t-butyl and $R_3$ is hydrogen.

7. The compound of claim 4 in which $R_1$ is methyl, $R_2$ is t-butyl and $R_3$ is bromine.

8. The compound of claim 4 in which $R_1$ is methyl, $R_2$ is t-butyl and $R_3$ is lithium.

9. A compound having the formula:

[Structure with O, $OR_1$, $OC(CH_3)_3$, $CO_2R_4$, $R_5$, $OR_1$ substituents]

wherein:
$R_1$ and $R_4$ are a $C_1$ to $C_6$ alkyl group or benzyl; and
$R_5$ is hydrogen, methoxy or acetoxy.

10. The compound of claim 9 in which $R_1$ is methyl and $R_5$ is hydrogen.

11. The compound of claim 9 in which $R_1$ is methyl and $R_5$ is methoxy.

12. The compound of claim 9 in which $R_1$ is methyl and $R_5$ is acetoxy.

13. A compound having the formula:

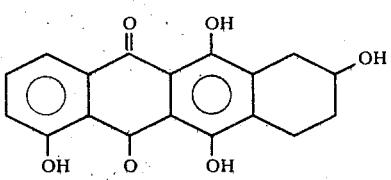

14. A process for the preparation of 5,8-di($C_1$–$C_6$) alkoxy-2-hydroxy-1,2,3,4 tetrahydronaphthalene with comprises hydrating 5,8-di($C_1$–$C_6$) alkoxy 1,4-dihydronaphthalene.

15. A process for the preparation of the ether, 5,8-di($C_1$–$C_6$)alkoxy 2-t-butoxy-1,2,3,4-tetrahydronaphthalene, which comprises etherification of the product of claim 14 with a t-butyl carbonium ion.

16. A process for the preparation of 5,8-di($C_1$–$C_6$) alkoxy-2-t-butoxy-6 or 7-(2-methoxycarbonyl) benzoyl-1,2,3,4-tetrahydronaphthalene which comprises brominating the ether of claim 15 followed by lithiation and acylation of the litho derivative with dimethyl phthalate.

17. A process for the preparation of 5,8-di ($C_1$–$C_6$) alkoxy-2-t-butoxy-6 or 7-(3-methoxy-2-methoxycarbonyl) benzoyl-1,2,3,4-tetrahydronaphthalene which comprises brominating the ether of claim 15 followed by lithiation and acylation of the litho derivative with dimethyl 3-methoxyphthalate.

18. A process for the preparation of 5,8-di($C_1$–$C_6$) alkoxy-2-t-butoxy-6 or 7-(3-acetoxy-2-methoxycarbonyl) benzoyl-1,2,3,4-tetrahydronaphthalene which comprises brominating the ether of claim 15 followed by lithiation and acylation of the litho derivative with dimethyl 3-acetoxyphthalate.

* * * * *